United States Patent [19]

Brown et al.

[11] Patent Number: 5,751,781
[45] Date of Patent: May 12, 1998

[54] APPARATUS FOR TREATING A PATIENT

[75] Inventors: Kevin J. Brown, Horsham; William R. Harwood, Hurst Pier Point; Terence Bates, Horsham, all of England

[73] Assignee: Elekta AB, Stockholm, Sweden

[21] Appl. No.: 726,287

[22] Filed: Oct. 4, 1996

[30] Foreign Application Priority Data

Oct. 7, 1995 [GB] United Kingdom ............... 9520567
Dec. 1, 1995 [GB] United Kingdom ............... 9524564

[51] Int. Cl.⁶ .................................................. A61N 5/01
[52] U.S. Cl. ......................... 378/65; 378/68; 378/69
[58] Field of Search ............................ 378/65, 64, 68, 378/69, 4, 20, 145, 147, 150, 152

[56] References Cited

U.S. PATENT DOCUMENTS

| | | | |
|---|---|---|---|
| 4,998,268 | 3/1991 | Winter | 378/65 X |
| 5,012,506 | 4/1991 | Span et al. | 378/152 |
| 5,044,006 | 8/1991 | Cyrulnik | 378/65 X |
| 5,117,829 | 6/1992 | Miller et al. | 378/65 X |
| 5,394,452 | 2/1995 | Swerdloff et al. | 378/65 |

FOREIGN PATENT DOCUMENTS

2728471A1 6/1996 France.
WO9428971 12/1994 WIPO.

Primary Examiner—David P. Porta
Attorney, Agent, or Firm—Jack D. Slobod

[57] ABSTRACT

A treatment source (4) such as a radiation source, is attached to the inner surface 50a of a drum 50, which drum 50 is mounted to a support (3) so as to be rotatable with respect to the support (3) about a central axis (R) displaced from the treatment source (4). The source provides a treatment beam (X) having a treatment beam axis (TB) extending through the rotation axis (R). A patient support (6) for receiving a patient (2) to locate a target treatment area (6) on the treatment beam axis (TB) is housed at least partially within the passageway defined by the inner surface 50a. The overall size of the apparatus is thus reduced. A preferred treatment technique, to which the apparatus may be adapted, is also described.

20 Claims, 8 Drawing Sheets

APPARATUS FOR TREATING A PATIENT

DESCRIPTION

1. Field of the Invention

This invention relates to radiotherapy apparatus for treating a patient.

2. Description of the Related Art

Figure 1:
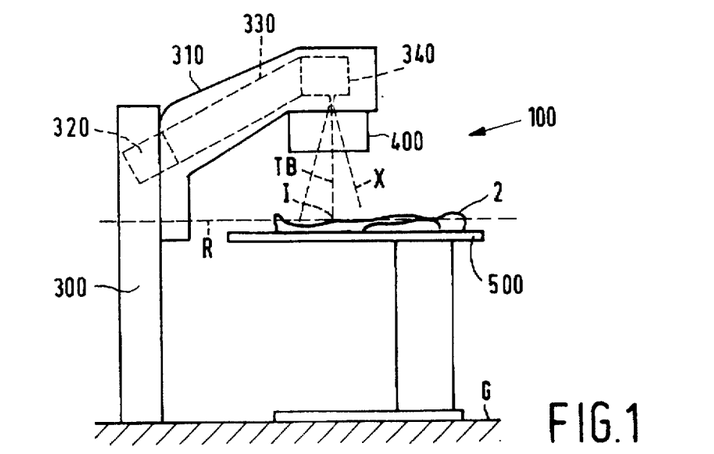
FIG. 1 shows a very schematic side view of a conventional radiotherapy apparatus.

FIG. 1 is a very schematic side view of one example of a known radiotherapy apparatus 100 which may, for example, be one of the range of SL series radiotherapy apparatus commercially available from Philips Medical Systems Radiotherapy, Crawley, England. As shown in FIG. 1, the apparatus comprises a support 300 placed on a suitable surface G to which a gantry 310 is mounted so as to be rotatable about a rotation axis R through substantially 360 degrees or more. The gantry 310 supports an electron source 320, a linear accelerator 330 which accelerates the electrons to a suitable high energy which may be in the region of 4 to 25 MeV (mega electron volts) and may be selectable. A beam deflection system 340 is provided to deflect the electrons through an angle of about or greater than 90 degrees to a treatment head 400 which includes a suitable target (not shown) onto which the electrons impinge to produce a beam X of high-energy X-rays directed along a treatment axis TB which is normal to the rotation axis R. The linear accelerator 330 and deflection system 340 are arranged to bring the electron beam to a focus F which effectively forms the source of the high energy radiation beam X. A patient 2 to be treated is supported on an independent patient support 500 which is placed on the surface G and is arranged to be accurately movable in directions parallel and perpendicular to the treatment beam axis TB to enable the desired treatment or target area of the patient 2 to be located at the so-called isocentre I, that is the location at which the rotation axis R and the treatment beam axis TB intersect, to ensure that the target area receives maximum radiation while the exposure to the radiation of the surrounding healthy tissue is kept as low as possible.

Recently, several techniques have been developed for radiotherapy treatment. One such technique, tomotherapy, involves a slice-by-slice treatment of a treatment area of a patient. Each slice is treated by a single gantry rotation, and the beams produced during the gantry rotation are constrained into a fan. Each ray of the fan beam is intensity modulated and every 5°, for example, of gantry rotation the intensity pattern is altered. A tomotherapy system also houses a diagnostic computer tomography (CT) imaging unit to provide verification.

The patient is stepped through the radiation field of the gantry, to enable the slice-by-slice treatment. Although this method enables an accurate dose distribution pattern to be developed, the indexing of the patient creates field matching problems, and the treatment time may be lengthy, since a complete gantry arc is required for the treatment of each slice.

An alternative approach is to use a beam which covers substantially the entire area to be treated, (a "broad beam") and the shape of the beam is modulated in two dimensions. A single gantry rotation is sufficient to enable treatment of the entire area. A multi-leaf collimator, such as that produced by Philips Medical Systems-Radiotherapy and as described in EP-A-314 214 which corresponds to U.S. Pat. No. 5,012,506 provides this two dimensional modulation. The present invention is concerned with treatments using such two dimensional shape modulated beams.

Although the apparatus of FIG. 1 operates perfectly satisfactorily, it occupies a relatively large area of space and moreover may be difficult to install in some buildings because of the nature of the access to the intended location for the apparatus. This may especially be the case where the apparatus is intended to replace an earlier machine such as a cobalt 60 source apparatus which requires less space.

SUMMARY OF THE INVENTION

It is an aim of the present invention to provide apparatus for treating a patient which may be more compact and so may be capable of being sited in smaller or more difficult access locations than previous apparatus.

According to the present invention, there is provided apparatus for treating a patient by exposing a treatment area of the patient to radiation, the apparatus comprising:

a support;

a hollow body having a central aperture which defines a passageway extending through the body, the hollow body being mounted to the support so as to be rotatable about a central axis of the hollow body;

a radiotherapy source mounted to the hollow body so as to be rotatable with the hollow body and for projecting a radiotherapy beam within the passageway which crosses the central axis of the hollow body;

a beam limiting device for controllably partially limiting the projected area of the beam; and a patient support for receiving the patient and which extends at least partly through the passageway and which is positioned such that an unlimited projection area of the beam substantially covers the treatment area of the patient.

Apparatus in accordance with the present invention enables the patient support to be at least partly accommodated within the space around which the treatment device, namely the hollow body, is to be rotated, so reducing the overall size of the apparatus in comparison to earlier apparatus.

The use of a hollow body to support the radiotherapy source (and other components) gives rise to a structurally stiff layout. The drum defined by the hollow body is strong and stable and will not easily deflect, improving mechanical accuracy and therefore treatment accuracy.

The radiotherapy source may include a linear particle accelerator disposed within the hollow body which extends in a plane which lies substantially perpendicular to a longitudinal axis of the patient support. Thus, the length of the particle accelerator does not contribute to the overall width of the treatment device, as is common in the prior art where the particle accelerator is frequently located in the gantry arm.

A beam deflecting means may be provided for deflecting the particle beam produced by the linear accelerator to a substantially radial direction with respect to the cylindrical passageway. Alternatively, the axis of the linear accelerator may intersect the central axis, avoiding the need for the beam deflecting means.

Preferably, the patient support is coupled to the hollow body and positioned at a location opposed to the radiotherapy source.

In this way, the apparatus does not require a separate support for the patient support, thus reducing the complexity of the apparatus.

Preferably, means is provided for allowing angular movement of the patient support about the rotation axis of the hollow body and for maintaining the patient support at a substantially constant attitude relative to a fixed reference plane. The angular movement of the patient support about the rotation axis coincides with the rotation of the hollow body so that the patient support is maintained at a constant distance from the radiotherapy source. This enables the patient support to be located at a lower position (for a certain angle of the hollow body) than would otherwise be possible because less clearance is required beneath the patient support to allow the passage of the treatment device during its rotation. This should facilitate the use of standard height patient trolleys for transferring bed ridden patients to the patient support so making this transferral process easier for the medical staff involved.

In order to maintain the patient support at a substantially constant attitude, the patient support is permitted to rotate about a lengthwise axis as the patient support moves angularly about the rotation axis of the hollow body. This means that the isocentre is defined by the intersection of the rotation axis of the patient support and the axis of projection of the beam.

The coupling of the patient support to the hollow body is preferably arranged to allow translational movement of the patient support with respect to the body in one or more directions parallel to or perpendicular to an axis of projection of the beam. This enables accurate positioning of the target treatment area at the isocentre.

The apparatus may further comprise an imaging radiation source which is also mounted to the hollow body, and a radiation detection device mounted to the hollow body at a location which is opposite to the imaging radiation source. In this way, the apparatus may carry out the image scanning procedure as well as the treatment procedure, and this may preferably be carried out in a single continuous operation. Preferably, the radiotherapy source is supplied by a megaelectron volt source whereas the imaging source is supplied by a kiloelectron volt source. The apparatus may also include a beam stop positioned opposite the treatment source, and/or a MeV imaging head which can provide verification of the treatment administered by the MeV treatment head during treatment.

The hollow body may comprise an inner portion within which is defined the passageway, and an outer portion, the inner and outer portions being rotatable with respect to each other, the radiotherapy source being mounted on the outer portion of the hollow body, and the beam limiting device being mounted on the inner portion of the hollow body.

In this way, the beam limiting device can be rotated from a treatment position during which it is aligned with the radiotherapy source. This will facilitate servicing of radiotherapy source.

Preferably, an imaging source is mounted on the outer portion of the hollow body at a position displaced from the radiotherapy source, the relative rotation between the two hollow body portions enabling the radiotherapy source or the imaging source to be aligned with the beam limiting device. In this way, imaging can be carried through the same beam limiting device as will be used for the treatment, so that accurate simulation of the treatment can be carried out.

The imaging source may comprise a light source, if insufficient funds are available for electronic imaging, but preferably the imaging source comprises an X-ray source, and the apparatus further comprises an X-ray image detecting device mounted on the inner portion of the hollow body, opposite to the beam limiting device.

The X-ray image detecting device may be slidably received by the inner portion of the hollow body so as to be slidable between a first position opposite to the beam limiting device and a second position displaced from the first position, the angle of displacement between the two positions corresponding to the angle of displacement between the imaging source and the radiotherapy source. In this way, the imaging detecting device may be positioned opposite the image source either with or without the beam limiting device interposed between the two. Thus, localisation of the treatment area can be carried out without the restriction of the beam limiting device, but beam limiting device may be used for image detection during simulation, and for verification during the treatment procedure.

As explained above, the apparatus of the invention is for treatment using a so-called "broad beam". One proposed radiotherapy treatment technique which uses two dimensional modulation of the beam shape involves delivering beams from a limited number, for example 5 to 7, of directions around the arc swept by the gantry. At each of these positions, the two dimensional shape of the delivered beam is modulated, for example using a multi-leaf collimator. Furthermore, the intensity of each elemental ray within the beam may also be modulated. This intensity modulation may be performed by altering a duty cycle of the leaves of the multi-leaf collimator. This technique uses a reduced number of treatment positions, and it is therefore necessary to optimise the dose distribution at each of these positions. As a result, it may be desirable to alter the angle of the patient support between treatment beams, so that each beam delivers an optimum treatment. Thus, oblique beam entry angles may be employed. It may alternatively be desirable to carry out the entire treatment with an oblique angle of the patient support. The apparatus according to the invention may be adapted to allow pivoting of the patient support with respect to the hollow body to permit such oblique entry angles. However, by virtue of the enclosed nature of the treatment volume within the passageway of the hollow body, the apparatus according to the invention is not ideally suited to patient manipulation during the treatment process.

The apparatus according to the invention is particularly suited to a treatment technique which is currently being developed by the Philips Medical Systems-Radiotherapy, in which a beam is produced at a large number of positions around a gantry arc of rotation (for example every 5°) with a fixed intensity beam being applied for the entire gantry arc. A number of gantry rotations are required to build up a complex intensity pattern.

Thus, the apparatus preferably comprises controlling means for providing a first beam of a first fixed intensity and controlling the beam limiting device to selectively limit the projection area of the beam at a variety of positions of the hollow body during a first rotation of the hollow body, and for providing a second beam of a second fixed intensity and controlling the beam limiting device to selectively limit the projection area of the second beam at a plurality of positions of the hollow body during a second rotation of the hollow body.

The controlling means may therefore continuously alter the shape of the fixed intensity beam during a rotation of the gantry (namely the hollow body) and in this way the change in patient set up between beams is not appropriate. The controlling means preferably comprises a computer system, as is known for controlling a multi leaf collimator.

The number of hollow body rotations that will be required will depend on the complexity of the intensity pattern which is desired to be implemented and this will depend partly upon the number of intensity peaks which are desired to be delivered.

The continuous nature of this treatment technique eliminates the need to provide for oblique entry angles so that access to the patient is not required during the treatment procedure. As a result, the apparatus of the invention may be particularly suited to the provision of such a treatment technique.

The invention also provides a method of operating the apparatus according to the invention so as to enable the above described treatment technique to be implemented.

As used herein, the term "projection area" should be interpreted as meaning the shape of the beam, in a plane perpendicular to the direction of projection of the beam, which has been transmitted through the beam limiting device.

The term "beam" should be understood to include not only the direction of continuous beams of particles or radiation, but also the direction of pulsed or discontinuous sequences of particles or radiation at a target area.

Finally, the term "attitude" means the angular orientation of the patient support about its lengthwise axis relative to the fixed reference plane.

BRIEF DESCRIPTION OF THE DRAWINGS

Embodiments of the present invention will now be described, by way of example, with reference to the accompanying drawings, in which.

It should of course be understood that the drawings are not to scale and that like reference numerals are used throughout the text to refer to like parts.

DETAILED DESCRIPTION OF THE PREFERRED EMBODIMENTS

Referring now to FIGS. 2 to 8 of the drawings, there is illustrated apparatus 1 for treating a patient 2, which apparatus comprises a support 3, which notably supports a hollow body in the form of a drum 50 having a cylindrical inner surface 50a defining a passageway. Of course, the passageway need not have a cylindrical inner surface, but can have any shape in which the patient support can be positioned. A treatment source 4 is mounted to the cylindrical surface 50a so that the treatment source 4 is rotatable about a rotation axis R displaced from the treatment source 4 and provides a treatment beam X having a treatment beam axis TB extending from the treatment device 4 through the rotation axis R. A patient support 6 for receiving a patient 2 is positioned so as to locate a target treatment area of the patient 2 on the treatment beam axis TB.

Apparatus 1 in accordance with the present invention enables the patient support 6 to be at least partly accommodated within the space around which the treatment device 4 is to be rotated, so reducing the overall size of the apparatus in comparison to earlier apparatus. The patient support 6 may be coupled to the inner cylindrical surface 50a of the drum 50, or to the support 3. In either case, the apparatus does not require a separate support for the patient support 6.

If, as is preferred, the patient support 6 is coupled to the inner surface 50a of the hollow body, the coupling is such as to maintain the patient support 6 at a substantially constant attitude with respect to a fixed reference plane. This coupling allows the patient support to be displaced from the rotation axis, and as a result, the overall diameter of the apparatus may be reduced, and this may, in the case of a linear accelerator (LINAC) radiotherapy apparatus, allow a straight through system to be used without increasing the size of the apparatus. A straight through system removes the need for a beam deflection system.

Figure 2:
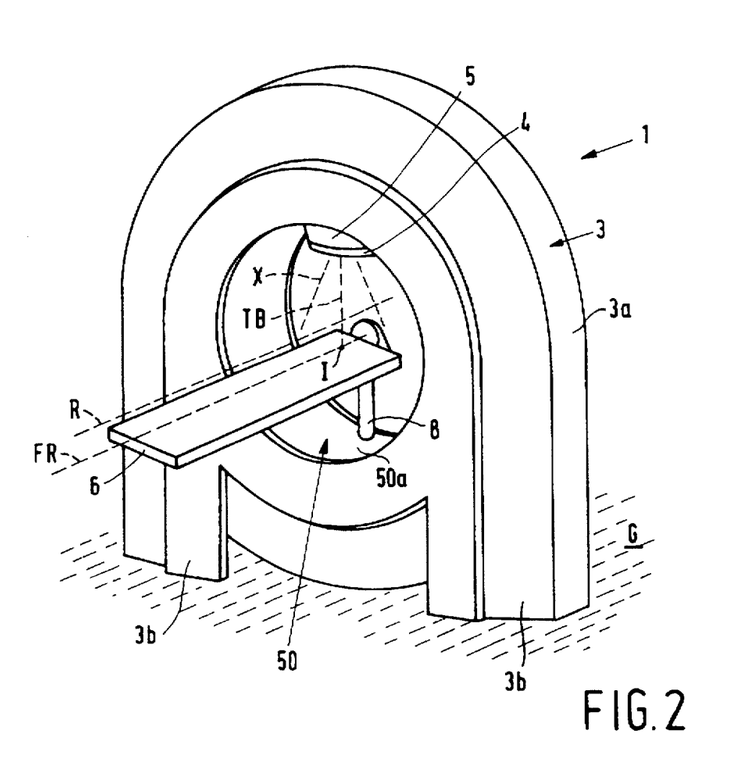
FIG. 2 shows a very schematic perspective view of one example of radiotherapy apparatus in accordance with the invention.
Figure 3:
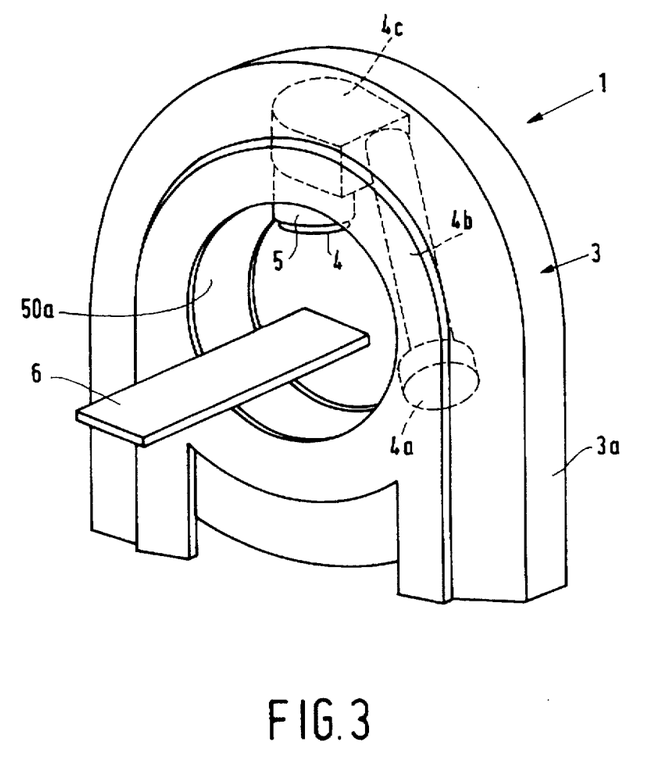
FIG. 3 shows a very schematic perspective view of the internal components of the apparatus shown in FIG. 2.
Figure 4:
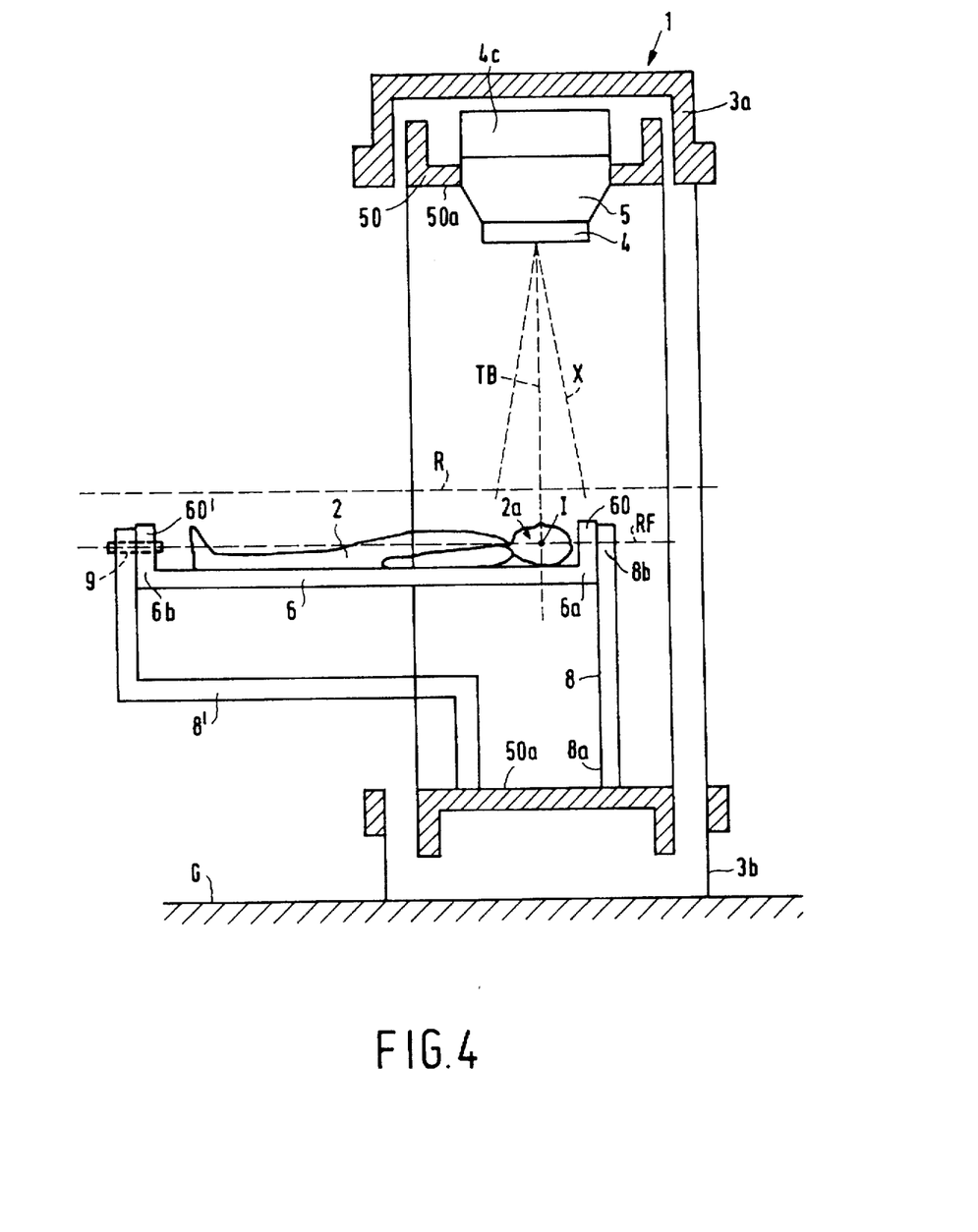
FIG. 4 shows a very schematic cut-away and part-sectional side view of part of the apparatus shown in FIG. 2.

FIGS. 2 and 3 are diagrammatic perspective views of one example of apparatus 1 in accordance with the invention. FIG. 4 shows a corresponding side view in which the support 3 and drum 50 have been shown cut-away to enable a clearer understanding of one possible construction.

In this example, the support 3 comprises a generally hollow cylindrical housing 3a having integral supporting members 3b which support the housing 3a on a surface, normally a suitably reinforced, generally ground or basement, floor of a building. In this example, a surface also forms the fixed reference plane G. The drum 50 is mounted using a conventional bearing arrangement (not shown) within the housing 3a and a drive arrangement (not shown) is provided for allowing the drum 50 to be rotated about its axis. The bearing and drive arrangements may be similar to those used in conventional radiotherapy apparatus, such as the SL series manufactured by Philips Medical Systems-Radiotherapy at Crawley, England. The drive arrangement may be a friction drive arrangement or a geared arrangement as will be briefly described below with reference to FIGS. 5 and 6.

The treatment source 4 is in this example a radiotherapy source comprising a high energy electron source 4a, associated LINAC 4b and treatment head 4 for producing a high energy X-ray beam X in a manner similar to that described above in relation to FIG. 1. As shown schematically in FIG. 3, the longitudinal axis of the LINAC 4b lies in a plane which is perpendicular to the longitudinal axis of the patient support 6. As a result, the overall width of the apparatus is kept to a minimum, and there is no need to provide extending gantry arms which have conventionally housed the required LINAC. As seen in FIG. 3, the LINAC 4b is positioned within the hollow body and lies in a plane substantially perpendicular to the length of the patient support. In this way, the LINAC does not contribute to the overall width of the apparatus. The LINAC also extends in a tangential direction, so that the diameter of the hollow body can be kept to a minimum. A beam deflection unit 4c is provided to direct the beam into a radially inward path towards the treatment head 4.

The treatment source 4 includes a beam limiting device, in the form of a multi-leaf collimator for example as described EP-A-314214. The multi-leaf collimator is capable of controlling the dose delivered to each elemental ray of the beam by controlling movement of the leaves. In this way, it is possible to create a two dimensional intensity pattern. The elemental rays typically have 1 cm×1 cm dimensions, the entire beam covering an area of 20 cm×20 cm. This beam area is generally sufficiently large to cover the treatment area of the patient.

Alternatively, the construction of the apparatus 1 may allow for the use of a shorter LINAC which can be provide straight through feed, removing the need for a beam deflection system 4c. In this case, the LINAC 4b is aligned with the treatment source 4.

The treatment source 4 is mounted using suitable conventional radiotherapy mounting techniques to the inner surface 50a of the drum 50 so that the housing 5 of the treatment source 4 is fixed in relation to the inner surface 50a of the drum 50. The treatment source 4 itself may of course be rotatably mounted within its housing 5 in known manner. The mounting is arranged to enable a treatment beam X to be directed normally of the rotation axis R so that the treatment beam axis TB intersects the rotation axis R.

The patient support 6 may be fixed with respect to the housing 3a, although with flexibility to position the support so that the treatment area of the patient coincides with the isocentre I. Thus, no alignment of the patient support is required at installation of the apparatus.

However, the patient support 6 is preferably mounted to the inner surface 50a of the drum 50 and is arranged so as to be diametrically opposed to the treatment source 4. As illustrated very schematically in FIG. 4, the patient support 6 is mounted to the inner surface of the drum 50 by means of a support member 8 which has one end 8a coupled to the inner surface 50a of the drum 50 and the other end coupled to a connection member 60 of the patient support 6 so as to enable the patient support 6 to rotate about a further rotation axis RF which is parallel to the rotation axis R. Rotation about the axis RF is required so that the patient support can maintain a constant attitude. Generally, although not evident from FIG. 2 or FIG. 3, the support member 8 will allow for translational movement of the patient support parallel and perpendicular to the treatment beam axis TB. The further rotation axis RF defines with the treatment beam axis TB the isocentre I at which the target area of the patient is to be located. The patient support 6 could be arranged to rotate about an axis coincident with the rotation axis R of the drum but, as will be evident from the discussion below with reference to FIGS. 6 to 8, the displacement of the further axis RF from the rotation axis R in a direction away from the treatment source 4 enables a more compact arrangement because a smaller clearance is required between the patient support 6 and the inner surface 50a of the drum 50 when the further axis RF is so displaced from the rotation axis.

If the further axis RF is made to coincide with the rotation axis R, then the patient support 6 will remain stationary in the centre of the cylindrical opening 50a. Such an arrangement is mechanically equivalent to an arrangement in which the patient support 6 is fixed to the housing 3a. This equivalence may be obtained by adjusting the position of the patient support 6, in the manner described in the following.

When the patient support is mounted to the drum 50 opposite to the treatment source 4, it provides a counter balancing weight to that of the treatment source, for all positions of the drum. This produces a stable structure. The location of the isocentre within the cylindrical passageway of the drum 50 also gives rise to a stable arrangement.

In addition, it may be desirable to position a beam stop opposite the treatment source. In conventional systems, although a beam stop may be desirable, it usually compromises the mechanical stability of the apparatus, since it requires a further gantry arm positioned opposite the treatment source gantry arm. In the apparatus according to the invention, the design of a beam stop may in fact result in more effective balancing of the apparatus. Alternatively or additionally, a MeV imaging source may be provided opposite to the treatment head, so as to provide treatment verification. This may also improve the balance of the apparatus.

The drum 50, support member 8 and associated couplings result in the patient support 6 being coupled to the treatment source 4 and may allow the position of the patient support 6 to be adjusted along the direction of the treatment beam axis TB and along the direction of the further rotation axis RF (and possibly also along a direction perpendicular to the treatment beam axis TB and the further rotation axis RF) to facilitate accurate positioning of the target area 2a at the isocentre I.

As indicated in FIGS. 2 and 4, the support member 8 is provided at one end (as shown the "head" end) 6a of the patient support 6. Although, a single support member 8 should generally be sufficient, if considered desirable, as illustrated very schematically in FIG. 4, a further support member 8' and associated connection member 60' may be provided at the other end (the "foot" end as shown) 6b of the patient support 6. Such a supplementary support member 8' would of course be constructed so as to cooperate with the support member 8 and be arranged to follow the movements of the support member 8. The support member or members may, of course, be positioned at any convenient location and could in some circumstances be movable relative to the inner surface 50a of the drum 50.

As the patient support 6 is coupled to the drum 50, it moves angularly about the rotation axis R. Rotation of the support 6 about the axis RF is designed to ensure that a constant attitude of the patient support 6 is maintained, as previously mentioned.

Any suitable arrangement may be used to enable the patient support 6 to be maintained at this substantially constant attitude, in this example parallel, with respect to the fixed reference plane G. In this example, the fixed reference plane G happens to coincide with the support surface upon which the apparatus is mounted.

Figure 5:
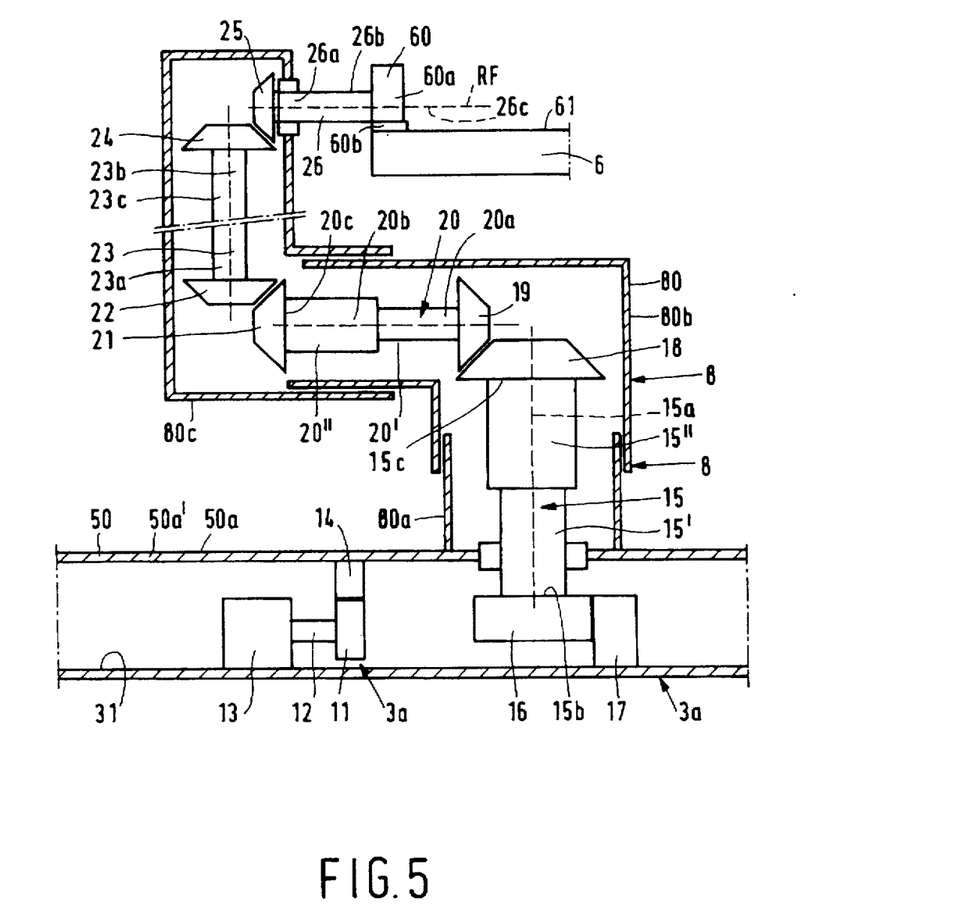
FIG. 5 shows a diagrammatic cut-away schematic side view of a portion of the apparatus shown in FIG. 2 for illustrating one possible way of controlling angular movement of the patient support.

One way of enabling the patient support 6 to be maintained at a substantially constant attitude is the use of a suitable gearing arrangement to control the angular movement of the patient support 6 in accordance with the rotation of the drum 50. FIG. 5 illustrates one possible gearing arrangement by way of a very schematic view of the appropriate part of the apparatus with the support member 8, the drum 50 and the housing 3a shown cut-away to enable the internal components to be seen.

In the example illustrated in FIG. 5, a drive wheel 11 is fixed against rotation to the output or drive shaft 12 of a motor 13 mounted to an interior wall or support 30 of the housing 3a. The drive wheel 11 meshes with a gear wheel or other suitable toothed surface 14 which circumscribes the interior 50a' of the inner surface 50a of the drum 50 so that operation of the motor 13 causes the drum 50 to rotate about the rotation axis R.

A first shaft 15 extends through the inner surface 50a of the drum 50 and is mounted by way of a suitable bearing or journal (not shown) so as to be capable of rotation about its longitudinal axis 15a. A lower end 15b of the first shaft 15 carries a gear wheel 16 which is fixed against rotation with respect to the first shaft 15. The gear wheel 16 meshes with a toothed surface or wheel 17 fixed to and circumscribing an interior cylindrical surface 31 of the housing 3a which is coaxial with the drum 50.

The other end 15c of the first shaft 15 carries a first bevel gear 18 which meshes with a second bevel gear 19 provided on one end 20a of a second shaft 20. The other end 20c of the second shaft 20 carries a third bevel gear 21 which meshes with a fourth bevel gear 22 carried by one end 23a of a third shaft 23. The other end 23b of the third shaft 23 carries a fifth bevel gear 24 which meshes with a sixth bevel gear 25 carried by one end 26a of a fourth shaft 26. The shaft 26 extends through and is rotatably journalled to the housing 80 of the support member 8. The other end 26b of the shaft 26 is fixed to the connection member 60 so that the axis 26c of the shaft 26 coincides with the further rotation axis RF.

Translational movement of the patient support 6 parallel or perpendicular to the treatment beam axis TB to allow the desired target area 2a to be precisely located at the isocentre I may be achieved by making the first and second shafts 15 and 20 telescopic as illustrated very schematically in FIG. 4 so that each shaft consists of two or more shaft members 15' and 15" and 20' and 20" and using an appropriate drive system such as the pneumatic or hydraulic arrangements commonly used in conventional LINAC radiotherapy apparatus or a worm gear train drive arrangement to effect relative movement of the telescoping shaft members.

In such a case, the associated shaft members 15' and 15" and 20' and 20" would of course be secured against relative rotation about their longitudinal axis by any suitable means. Thus, for example, the shaft members 15' and 15" and 20' and 20" may be of non-circular cross-section so as to allow only relative longitudinal movement and not relative radial movement or may be provided with corresponding longitudinally extending tongues and grooves which engage to prevent relative radial motion but allow relative longitudinal movement of the respective shaft members 15' and 15" and 20' and 20".

Such an arrangement allows for the height or position of the patient support 6 along the treatment beam axis TB to be adjusted and also allows for movement of the patient support 6 along the rotation axis R to position the correct target area 2a within the path of the beam X and at the isocentre I.

To adjust the further rotation axis and thus the isocentre I relative to the patient support 6 to compensate for different sizes or bulks of patients 2, the further rotation axis RF may be made movable with respect to the surface 61 of the patient support 6 by, for example, forming the connection member 60 as two or more telescopic members 60a and 60b, as illustrated schematically in FIG. 4, which, in a manner similar to the shaft members 15' and 15" and 20' and 20", allow relative longitudinal but not relative rotational movement, and by using an appropriate drive arrangement as discussed above.

The housing 80 of the support member 8 is formed of correspondingly telescoped housing parts 80a, 80b and 80c to accommodate telescopic movement of the shaft members 15' and 15" and 20' and 20". As will be appreciated, the shaft 23 should be of sufficient length to provide clearance for rotation of the patient support 6.

With such an arrangement, operation of the drive arrangements for the telescopic shafts 15' and 15" and 20' and 20" (and 60a and 60b, if present) allows the desired target area 2a of the patient 2 to be located precisely at the isocentre I. Operation of the motor 13 causes the drum 50 to rotate about the rotation axis R. This rotation results, by way of the combination of gear wheels 16 and 17, in the rotation about its longitudinal axis 15a of the first shaft 15 so causing, by virtue of the meshing of the bevel gears 18 and 19, the second shaft 20 to rotate about its axis 20b which, by virtue of the meshing of the bevel gears 21 and 22, causes the third shaft 23 to rotate about its axis 23c which in turn, by virtue of the meshing of the bevel gears 24 and 25, causes the fourth shaft 26 to rotate about its axis 26c, so causing the patient support 6 to rotate about the further rotation axis RF and thus to effect angular movement about the rotation axis R. With the appropriate gear ratios, which may generally be 1:1, the gearing arrangement causes the patient support 6 to maintain a constant, in this case a horizontal, attitude with respect to the fixed reference plane G. Such an arrangement allows control over the rotation of the patient support 6 and allows, if desired, the constant attitude to be other than horizontal.

Where, as mentioned above in relation to FIG. 2, a supplementary support member 8' is provided, the construction and coupling of that support member 8' may be similar to those of the main support member 8 and operation of the telescoping arrangements will of course be controlled so as to maintain the constant attitude of the patient support 6. Of course, the rotational coupling between the supplementary support member 8' and the supplementary connection member 60' may be simply a pivot pin 9 (as shown in phantom lines in FIG. 4) which allows the coupling to follow the driven rotation at the other end 6a of the patient support 6.

Although not shown, another possible gearing arrangement would be to mount the patient support 6 within a large gear wheel having its axis of rotation coincident with the further rotation axis RF and using an appropriate gear train drive gear to rotate the gear wheel. The gear wheel need not necessarily form a complete circle but need only be segment of a circle of sufficient extent to allow the required degree of rotation of the patient support 6 about the further rotation axis RF. Such a gear wheel could be displaced from the line of sight of the treatment source 4. In such a case, the patient support 6 may be mounted to the gear wheel so as to be slidable in a direction parallel to the axis of rotation RF and the gear wheel itself may be arranged, in a manner similar to that described above, so as to be movable in a direction parallel to the treatment beam axis TB to able accurate positioning of the target area 2a at the isocentre I.

Figure 6:
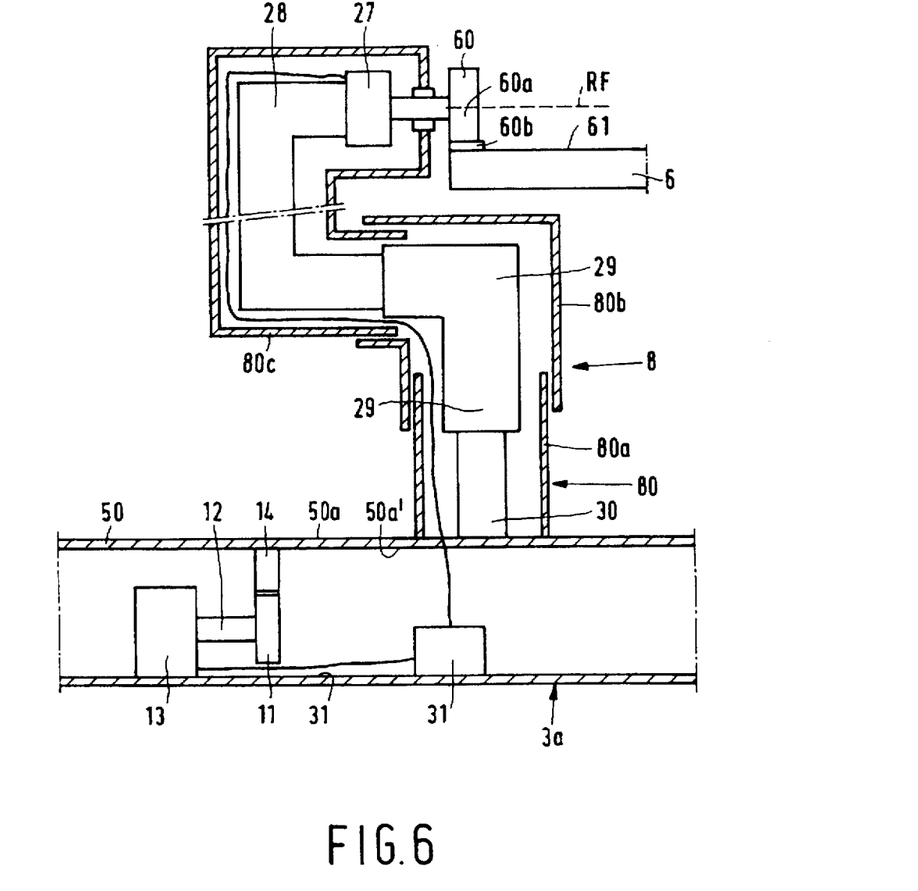
FIG. 6 shows a diagrammatic cut-away schematic side view of a portion of the apparatus shown in FIG. 2 for illustrating another possible way of controlling angular movement of the patient support.

FIG. 6 shows a view similar to FIG. 5 of an alternative arrangement for enabling the patient support 6 to be maintained at a substantially constant attitude. This arrangement differs from that described above in relation to FIG. 4 in that the gear trains are dispensed with and rotation of the patient support 6 is controlled by a separate motor 27 mounted to a shaft 28. In order to allow translational movement of the patient support 6, the shaft 28, which is generally U-shaped, forms a first telescopic arrangement with a further generally U-shaped shaft 29 which itself forms a second telescopic arrangement with another shaft 30 having its other end mounted to the housing 80 or the surface 50a. The telescopic arrangements are controlled as discussed above with reference to FIG. 4 and operation of the motor 21 is controlled electronically in accordance with the operation of the motor 13 by appropriate controls 31 coupled between the motors 13 and 27.

As can be seen from the Figures, the arrangement of FIG. 6 operates in a similar manner to that shown in FIG. 5 except that the function of the gear train is performed by the motor 27 which is a servo-following motor driven in response to the motor 13. This avoids the need for gear trains which are subject to wear and also, potentially, backlash and facilitates the use of computer control of the apparatus 1 which should enable greater precision.

As another possibility, the patient support 6 may be made sufficiently heavy to cause it to rotate about the further axis RF to maintain a horizontal attitude simply under the influence of gravity. In such a case, the motor drive shown in FIG. 5 may simply be omitted so that the shaft 28 provides a pivot pin to which the connection member is journalled to allow the patient support 6 to rotate about the further axis RF under the influence of gravity. Suitable damping may be provided by, for example, friction, hydraulic or pneumatic means. Such an arrangement is relatively cheap and simple to manufacture.

Figure 7:
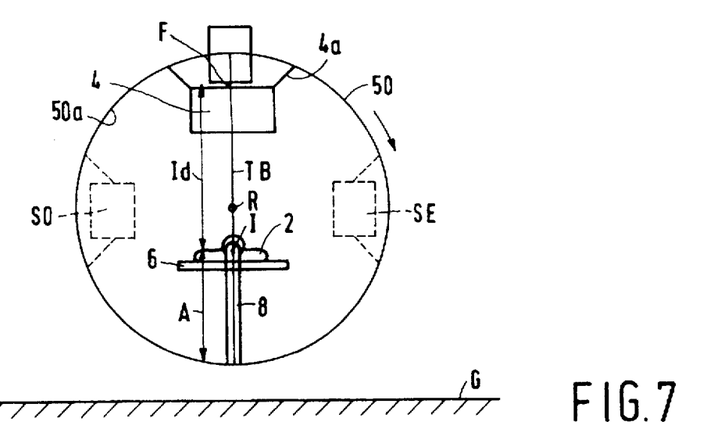
FIGS. 7 to 9 are diagrammatic sketches for illustrating the operation of the apparatus shown in FIG. 2.
Figure 8:
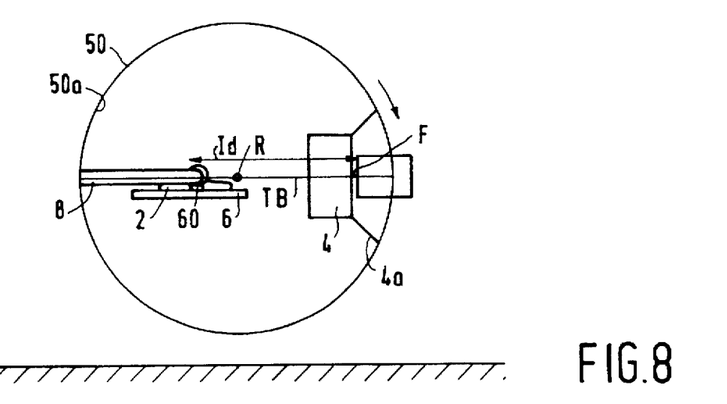
Figure 9:
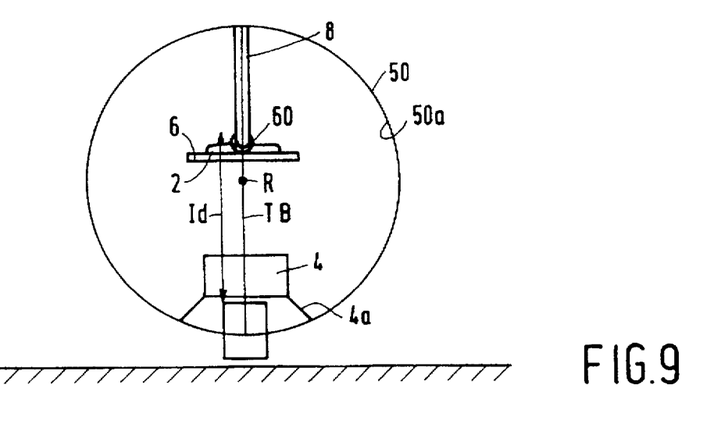

FIGS. 7 to 9 are schematic diagrams for illustrating the operation of the apparatus 1 described above as the treatment source 4 rotates.

FIG. 7 shows the apparatus 1 in a starting condition with the treatment source 4 above the patient support 6. In this example, the radial distance A from the inner surface of the drum to the isocentre I is taken to be 80 cm (centimetres) while the isocentric distance $L_d$ from the isocentre I to the X-ray target indicated as F in FIGS. 6 to 8 is 100 cm and the height of the LINAC (or the beam deflection system where a straight through LINAC is not used) is 40 cm in total with 20 cm of that total being outside the drum 50 in the spacing provided by the housing (not shown). The clearance of the drum 50 above the fixed reference plane G is 20 cm.

FIG. 8 illustrates the situation when the treatment source 4 has rotated 90 degrees clockwise from the position shown in FIG. 7 while FIG. 9 illustrates the situation when the treatment source 4 has rotated 90 degrees clockwise from the position shown in FIG. 8 As can be seen from these Figures, the pivotal coupling between the support member 8 and the patient support 6 and any associated drive arrangement cause the patient support 6 to maintain a constant attitude despite the rotation of the drum 50. Thus, in the example shown, the patient support 6 remains horizontal and is thus substantially parallel to the support surface which also forms the fixed reference plane G in this case with, of course, the patient 2 uppermost.

Also, as can clearly be seen from FIGS. 7 to 9, the fact that the isocentre I does not need to be coincident with the axis of rotation R means that the patient support 6 and the isocentre I are further from the support surface G in the position shown in FIG. 8 than in the position shown on FIG. 6 so facilitating passage of the treatment source 4 beneath the patient support 6. Thus, this apparatus requires less clearance between the drum 50 and the supporting floor G than is required between the floor and gantry of conventional radiotherapy apparatus. This allows the patient support 6 to be located at a lower position than would otherwise be possible and thus should facilitate the use of standard height patient trolleys for transferring bedridden patients to the patient support 6 so making this transferral process easier for the medical staff involved.

Systems have been provided in which a channel is set into the floor so that the rotating gantry arm can pass beneath floor level. This allows the apparatus to be positioned lower down, so facilitating access to the patient and the use of patient trolleys. However, when manipulation of the patient is desired, the channel may provide a hazard to the operator. As discussed above, the apparatus of the invention, when incorporating a patient support which is displaced from the rotation axis, allows the patient support to be positioned lower down, for some angles of rotation of the hollow body. In addition, it may be possible to use the reduction in the diameter of the drum to enable a straight through LINAC to be used. This may increase the diameter of the drum, and it may therefore still be desirable to set the apparatus in a channel in the floor. As a result of the enclosed nature of the apparatus of the invention, the channel in the floor will not be exposed to the operating staff, since there are no gantry arms. Thus, any hazards or inconvenience normally associated with such an arrangement are avoided.

The space between the drum 50 and the housing 3a may be used to accommodate control equipment of the apparatus so allowing for a very compact arrangement.

As described above, the patient support 6 may remain stationary within the passageway defined by the cylindrical wall 50a. This may be achieved either by fixing the support 6 to the housing 3a, or, when the support is fixed to the inner surface 50a of the drum 50 as described above, by suitable positioning of the patient support 6. This may be desired if an imaging arrangement is also provided on the inner surface 50a of the drum 50.

Such an arrangement is known in the art and comprises a KeV imaging source 50 which in the apparatus of the invention is located at one point around the drum, and an image sensor SE located diametrically opposite the imaging source.

The imaging source SO and sensor SE could be provided at 900° to the treatment source 4, again balancing the rotating drum 50, as shown in phantom lines in FIG. 7. In such a case, it is essential for the patient support to remain stationary at the rotation axis R during the image sensing procedure. As described above, this may be achieved by appropriate positioning of the patient support 6.

A system may be desired in which simultaneous imaging and treatment are provided, preferably with verification by having a MeV imager opposite the treatment head. In this case, it is preferred that the patient is permanently located on the rotation axis.

Generally, the attitude of the patient support should remain constant with respect to a plane G extending at a given angle, generally perpendicularly, to the treatment beam axis TB and thus the fixed reference plane should really be considered to be fixed with reference to the treatment beam axis TB. However, as indicated above, in most cases the fixed reference plane will be the horizontal and will be generally parallel to the plane of the support surface on which the apparatus is stood and so that support surface can be considered to be the fixed reference plane.

Although in the above-described examples, the treatment source 4 comprises a high energy X-ray radiation source for directing a beam X of radiation at the target area 2a of the patient 2, the present invention may be applied to apparatus using gamma radiation or particle radiation. Also, of course, the treatment beam need not necessarily be continuous but could be pulsed or discontinuous.

Figure 10:
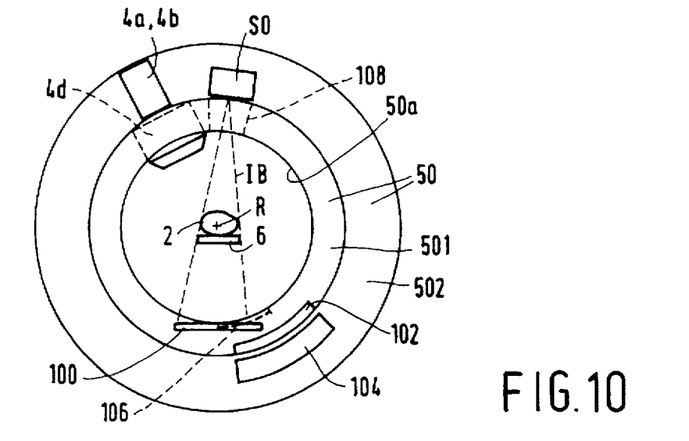
FIG. 10 shows a second example of radiotherapy apparatus in accordance with the invention, during an imaging mode of operation.
Figure 11:
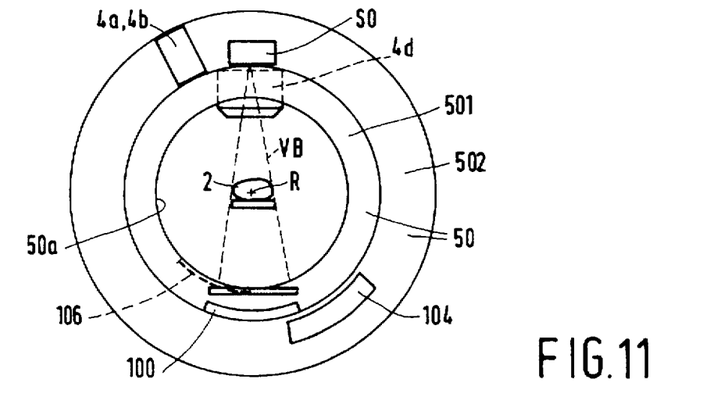
FIG. 11 shows the radiotherapy apparatus of FIG. 10, during a simulation mode of operation.
Figure 12:
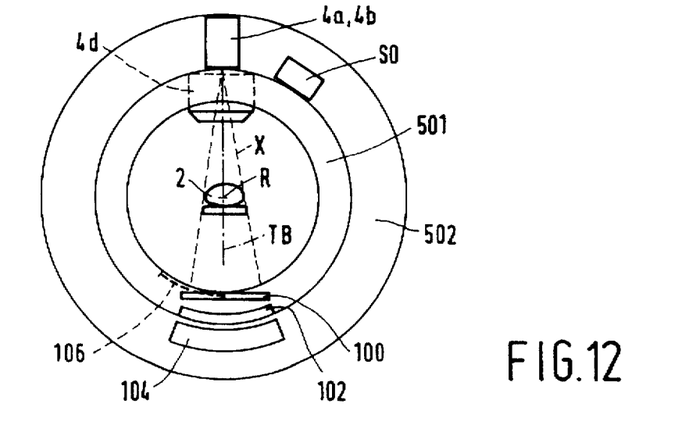
FIG. 12 shows the radiotherapy apparatus of FIG. 10, during a treatment mode of operation.

A second example of radiotherapy system according to the invention is shown in FIGS. 10 to 12. The same reference numerals are used for components in common with the first embodiment. The hollow body 50 and mounted components only are shown, but the hollow body 50 is to be rotatably mounted to a support as in the first embodiment, and a patient support 6 is also provided. The apparatus of the second embodiment is particularly for providing tumour localisation as well as treatment, and therefore, as discussed above, the patient support 6 is preferably stationary on the rotation axis R of the hollow body 50. This is most easily achieved by fixing the patient support 6 to the support of the hollow body. Again, the patient support 6 may have some freedom to rotate about a vertical axis, to allow oblique treatment angles. Of course, it is possible to provide coupling of the patient support to the hollow body as described in relation to the previous example, if desired.

Once more, the hollow body 50 is in the form of a drum having an inner surface 50a defining a passageway. The passageway may have a cylindrical inner surface, but can have any shape in which the patient support 6 can be positioned. The treatment source 4 is mounted to the drum so that the treatment source 4 is rotatable about a rotation axis R displaced from the treatment source 4 and provides a treatment beam X having a treatment beam axis TB extending from the treatment device 4 through the rotation axis R. The patient support 6 for receiving a patient 2 is positioned so as to locate a target treatment area of the patient 2 on the treatment beam axis TB.

The second embodiment provides a modular arrangement of components of the radiotherapy system, so that the system can be tailored to the expertise or finances of a particular user. For example, the finances available to some countries may prohibit the use of a sophisticated Computer Tomography scanning system, or the use of a treatment device using expensive multi-leaf collimators and the associated control systems.

Radiotherapy systems do exist which provide less advanced treatment programs than those possible using advanced computer tomography generated images and multileaf collimator generated beam shapes. However, even these systems include a separate localising apparatus and treatment apparatus. Thus, a localising apparatus is provided for localising a treatment area of a patient, namely the area to be irradiated, by using a KeV radiation source and imaging device. This may involve providing an imaging beam at, for example, two or four positions around the patient. This then enables the desired treatment beam shape to be determined for those angles. The localising apparatus also enables simulation to be carried out, which involves adjusting a collimator to provide a beam limiting function which generates the desired treatment beam shape. In order to verify the beam shape produced by the collimator, a light source may be provided so that visible adjustment of the collimator can take place.

The collimator used is generally a device which enables only a rectangular beam limiting function to be achieved. The use of a multileaf collimator for the treatment, which is a more expensive apparatus and necessitates expensive control algorithms and more experienced operators, may not be financially possible.

In a more advanced system where the treatment is to involve the use of a multileaf collimator, the collimator used for simulation with the KeV imaging source will not be of the same type as that used for the treatment, and a multileaf collimator is generally not used for treatment simulation at all. Furthermore, a MeV treatment collimator requires leaves of significant depth to absorb the high energy radiation which is to be blocked, which leads to a very heavy treatment collimator with accordingly powerful control systems. Since this high level of radiation absorption is not required of the collimator for simulation of the collimator settings, a different, less expensive, beam limiting device is used for simulation.

Having determined the collimator positions for the different treatment beams, a separate treatment apparatus, having a MeV radiotherapy source, is used for the radiotherapy treatment.

The apparatus of the first embodiment of the invention enables the imaging arrangement to be provided in the same apparatus as the treatment head, so providing the possibility of sequential scanning and treatment, without repositioning the patient. The apparatus of the second embodiment has further benefits, particularly relating to simulation and verification of the treatment, as will be explained in the following description of the specific features of the second embodiment.

As shown in FIG. 12, the hollow body 50 comprises an inner portion 501 and an outer portion 502, the two portions being rotatable with respect to each other by appropriate mechanical interconnection. The collimator 4d (beam limiting device) is provided on the inner portion 501 of the hollow body, and an image detection device 100 is provided opposite to the collimator. The image detection device 100 may comprise a light sensing array which has a surface which converts the incident X-Ray or other radiation into light for detection by the light sensing array.

A beam stop 102 is also provided on the inner portion 501 in order to act as a counterbalance for the collimator 4d. Although the image detection device 100 is located opposite to the collimator 4d, it has a much lower weight than that of the collimator, and an additional counterbalancing weight is therefore preferred.

The outer portion 502 of the hollow body houses the radiotherapy source 4a,4b, which may be a 6 MeV X-ray radiation source. This may be a straight through X-ray source 4a and LINAC 4b (as represented in FIGS. 10 to 12), but it may comprise an arrangement similar to that shown in FIG. 3 including a beam deflection unit. Again, a beam stop 104 is provided opposite to the MeV source to act as a counterbalancing weight to balance the outer portion 502 of the hollow body 50.

A KeV imaging radiation source SO is also mounted to the outer portion 502 of the hollow body, preferably adjacent the treatment source 4a, 4b. Since the outer portion 502 can rotate relatively to the inner portion 501 of the hollow body, either the treatment source 4a, 4b or the imaging source SO can be aligned with the collimator 4d. Furthermore, the imaging device 100 is preferably mounted on bearings 106 (only represented schematically) so as to allow movement of the imaging device 100 relatively to the inner portion 501 of the hollow body 50, so that movement is possible between a first position (FIG. 12) in which the imaging device 100 is opposite the collimator 4d, and a second position (FIG. 10) in which the imaging device 100 is offset from the first position. Alternatively, the image detecting device 100 may be mounted on its own drum arrangement rotatable relatively to the inner portion 501.

The operation of the device shown in FIGS. 10 to 12 will now be described. FIG. 10 shows the device in an initial imaging mode of operation. The imaging device 100 is offset from the position opposite the collimator 4d, so that an image scanning operation may be carried out using an imaging beam IB which is not obstructed by the collimator 4d. Both portions of the hollow body 501, 502 may be rotated together in order to obtain images from a number of positions around the patient. The imaging source is preferably displaced from the treatment head 4a, 4b around the outer portion 502 only by an angle sufficient to ensure that the collimator 4d does not obstruct the path of the imaging beam IB during the imaging shown in FIG. 10. By reducing the displacement of the two components to a minimum, the relative movement between the inner and outer portions 501, 502 of the drum is kept to a minimum.

Based on the detected images, the collimator settings for treatment from the selected positions around the patient 2 may be evaluated. In FIG. 11, the imaging device 100 has been returned to the position opposite the collimator 4d. In addition, the outer portion of the hollow body has been rotated so that the KeV imaging source SO is now aligned with the collimator 4d. This enables verification of the collimator settings using the image sensing device (rather than by visual inspection). A verification beam VB is therefore transmitted through the collimator 4d. The collimator positions can be accurately verified as corresponding to the desired treatment. It is possible to omit the provision of movement of the image detection device 100 relatively to the inner portion 501 of the hollow body, if desired. For example, the image scanning may be provided by projecting the imaging beam IB through an open collimator, and only setting the collimator to limit the projection of the beam for verification of the treatment plan.

During the treatment procedure, shown in FIG. 12, the treatment source 4a, 4b is aligned with the collimator 4d. The image detection device 100 provides simultaneous treatment verification. Again, the two portions 501, 502 of the hollow body 50 rotate together to enable treatment from the selected angles around the patient 2.

The apparatus of this embodiment may be supplied with different equipment levels. For example, a basic system could be supplied to users who had previously found the cost of two separate units, namely the simulation apparatus and treatment apparatus described above, to be prohibitive. In this case, the apparatus could comprise only a treatment source 4 and simple rectangular collimator 4d. The initial localisation could be carried out by feel, as is already sometimes practised. Following this identification of the treatment area, treatment planning could be carried out by using a light source in place of the KeV imaging source, to provide visual adjustment of the treatment beam area. This system has the benefit of the integrated patient support 6, not requiring stepping of the patient through the treatment area, and enables at least basic visual treatment planning together with conventional radiotherapy treatment from a single machine. The use of a beam stop 102, 104 as a counterbalancing weight reduces the amount of shielding required for the treatment room, which reduces the installation costs. The installation is also simplified because of the use of a stationary patient support 6, which may therefore be a fixed part of the apparatus. Thus, this configuration can be considered to provide a lowest cost complete radiotherapy apparatus for use in, for example, developing countries.

This system could be supplied or could be upgraded to include the KeV imaging source SO and image detector 100. This then enables more accurate treatment planning by enabling electronic image scanning. Furthermore, when an image detector 100 is provided, the possibility of simultaneous verification during treatment becomes possible, because the relative rotation of the two portions of the hollow body 501, 502 enables the imaging device 100 to be located opposite to the imaging source SO for imaging or opposite to the treatment source 4 for verification.

The use conventionally of two separate apparatus for localisation/simulation and for treatment has the effect that simulation of the treatment is carried out through a different collimator to that used for the treatment itself. The apparatus of this embodiment, in addition to reducing costs by providing a single collimator, also has the advantage that the treatment simulation is carried out using the same collimator as that used for the treatment itself. This enables the treatment beams to conform exactly with the simulated treatment, and differences in the beam shapes do not arise as a result of the different collimator configurations. Previously, it would not be considered appropriate to provide a MeV collimator in a simulator apparatus having a KeV imaging source.

A more advanced system, or a further upgrade, could include a Computer Tomography scanning system, to provide a more accurate evaluation of the tumour shape. The use of a multileaf collimator would then enable a treatment program to be sufficiently advanced to warrant this scanning system.

The radiotherapy system of this invention may be provided as a transportable system as a result of the unitary construction. The use of the beam stops 102, 104 should enable sufficient shielding to be possible in a lorry compartment, so that the system may be provided as an assembled transportable unit. This may enable the system to be shared between regions which would not individually have the finances or required level of expertise to install and operate such a system.

The inner portion of the hollow body 501 may include an opening 108 (shown in FIG. 10 only) which, when aligned with the treatment source (and imaging source), enables servicing of the treatment source (and imaging source) without removal of the collimator. Previous systems have required removal of the collimator in order to gain access to the treatment head, which requires regular servicing. As explained above, a MeV multi-leaf collimator comprises heavy components to achieve the required level of beam absorption, and may typically weigh approximately ½ ton. The apparatus of the second embodiment therefore reduces servicing costs, avoiding the need to remove the collimator. The opening 108 may also function as a passageway for the imaging beam IB through the inner portion 501 of the hollow body, as shown in FIG. 10.

The different levels of equipment enable the system to be adapted to any level of treatment, from a basic system which would normally be used for palliative treatment, to an advanced Cone Beam Computer Tomography system. One treatment technique, under development by the applicant, may be applied by the apparatus of either embodiment of the invention, and is discussed in the following.

Various radiotherapy treatment techniques have evolved using apparatus similar to that shown in FIG. 1.

One such technique, tomotherapy, involves a slice by slice treatment (and image scanning) of a tumour. A required dose distribution pattern is obtained for each slice and this dose is administered by the application of a fan shaped beam. The treatment of each slice involves a single gantry rotation with different fan shaped beams being applied at different gantry angles. The patient is stepped through the radiotherapy apparatus to enable treatment of the entire treatment area. Although a very accurate dose distribution pattern may be obtained, problems may arise in matching the radiation fields of adjacent slices and a prolonged treatment time may result if a large number of slices are involved.

This invention is concerned with an alternative approach in which the radiotherapy beam covers substantially the entire tumour area. Thus, instead of a fan beam being propagated which penetrates into a slice of the patient, the beam covers a two dimensional, for example square, area and the envelope of the radiation beam may be considered to be a square based pyramid, for example. As a result, a single rotation of the gantry, or in the case of the present invention of the drum, enables a dose to be administered to the entire treatment volume of the patient. The distribution pattern of the two dimensional area covered by the beam is controlled by a multi-leaf collimator or other collimator (beam limiting device) which provides two dimensional limitation of the beam shape, for example into a rectangular shape of the selected dimensions.

A proposed treatment technique which operates according to this principle delivers these beams from a limited number, for example 5 to 7, of directions. Each of these beams has its intensity modulated for each elemental portion of the beam area with the result that a sufficiently accurate dose distribution may be obtained from the limited number of beam delivery positions. However, each of the limited number of beams will have a complex dose distribution pattern which may take a long time to administer. This is particularly so as the intensity is varied by altering the duty cycle of the leaves of the multi-leaf collimator. Furthermore, in view of the limited number of beams to be generated, an optimum distribution pattern is desired for each of those beams to enable the overall dose distribution to have the required accuracy. In view of this, it is desirable to alter the adjust patient position between beam deliveries since an oblique entry angle may be desired, or an oblique angle may be required for the entire treatment. As a result, it may be necessary to provide an area of clearance around the patient to enable the operating staff to carry out set up positioning during the treatment procedure. Although the apparatus according to the invention may be used to implement such a treatment technique, for example the patient support 6 may be rotatable about the support member 8, the apparatus of the invention is more suited to a treatment technique which does not require patient manipulation during the treatment procedure. This is a result of the enclosed nature of the apparatus according to the invention. For example, the technique above may be employed, without providing oblique entry angles.

As explained above, the apparatus of the invention and particularly the second embodiment is suitable for a range of different treatment techniques according to the different types of imaging system and treatment heads that may be employed. However, in the field of advanced treatment techniques, involving computer generated scanning images and complex beam distribution patterns, the apparatus according to the invention is particularly suited to an alternative treatment technique currently being developed by the applicant.

This new technique uses multi-leaf collimator shaped fields which change shape during rotation of the drum in order to deliver the dose to the treatment target. The fields have a fixed intensity during the rotation of the drum and a number of drum rotations are required in order to build up a complex intensity pattern. Thus, the treatment is delivered as a number of arcs each with a different succession of field shapes, and the shapes are defined typically every 5°. The number of arcs required in order to define the intensity distribution pattern may be of the order of 5 and a single rotation of the hollow body may take of the order of 4 minutes. In particular, during the rotation of the hollow body, the multi-leaf collimator does not carry out intensity modulation but merely changes the shape of the beam delivered.

The overall intensity distribution must be reduced into individual intensity distributions for each beam delivery gantry angle. Each of these individual distributions is then reduced into portions which correspond to the beam shapes which may be delivered by the leaves of the multi-leaf collimator. It may be required to rotate the collimator between angles of the hollow body since there are certain collimator angles along which the multi-leaf collimator leaves best conform to the required field shape.

Once the intensity distribution for a particular leaf of the multi-leaf collimator is known for a particular position, it is necessary to define the intensity distribution as a combination of intensity patterns that can be applied by the multi leaf collimator (namely continuous strips) which may be successively applied.

Figures 13A, 13B:
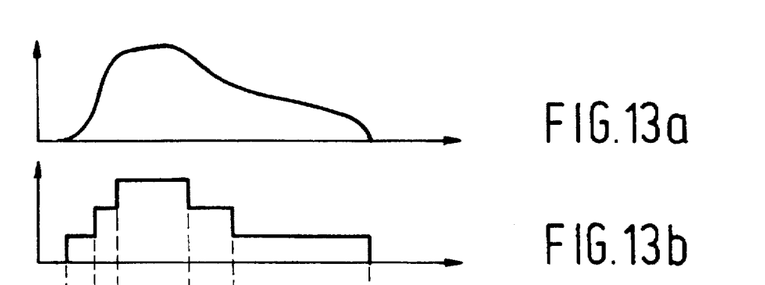
FIG. 13 is a diagram explaining the preferred treatment technique.
Figure 13C:
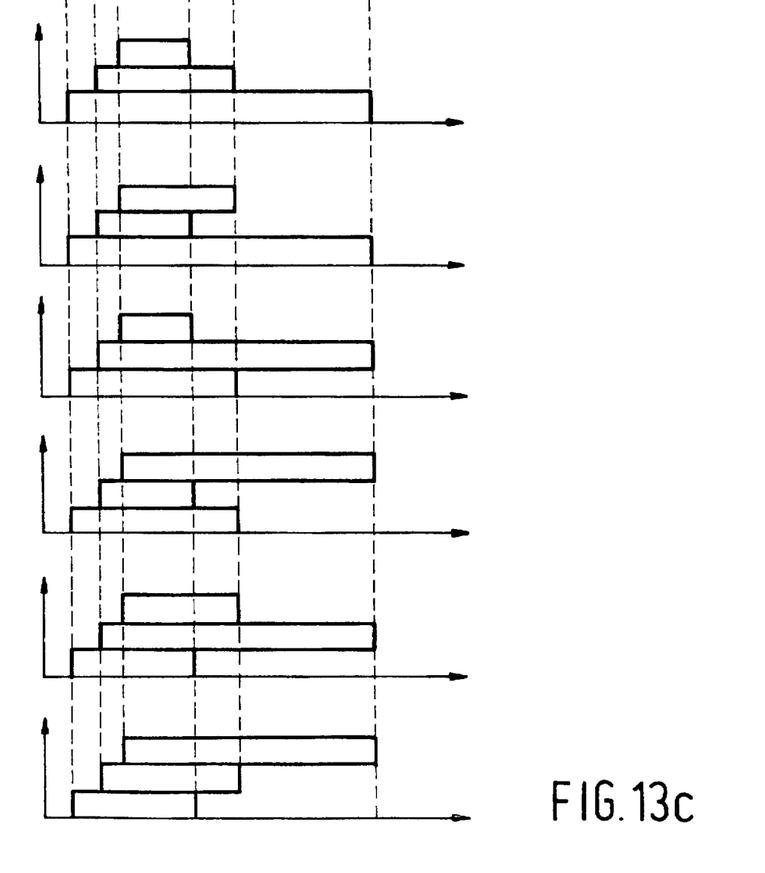

This principle is best explained with reference to FIG. 13. FIG. 13 part (a) shows a desired intensity profile, to be delivered from a certain drum angle, along a strip defined by one pair of leaves of a multi-leaf collimator. As shown in FIG. 13 part (b), the desired intensity may be approximated as a stepped profile which in this case has three different intensity levels. I to reduce this intensity profile into the profile to be applied by successive leaf positions during successive arcs of the treatment, there are a number of possible solutions. Each of these solutions is shown in FIG. 13 part (c). There is also freedom to choose the order in which the constituent portions are applied.

The fact that there are a number of ways of obtaining the desired intensity profile over the number of arcs enables leaf positions to be chosen which reduce the movement of the leaves of the multi-leaf collimator during the rotation of the drum. The process shown in FIG. 13 assumes that the same intensity is applied for each arc of treatment. However, different intensities may be applied during the different drum rotations and this will alter the manner in which the desired intensity profile is decomposed.

Some leaf pairs will need to be closed at certain points around the arc and it is arranged so that the closure of the two leaves is located at the edge of the collimator area, since the closure of two leaves cannot completely prevent the passage of radiation. To prevent excessive movement of the leaves, the previous and following decomposition pattern will be appropriately selected to minimise the required travel path of the leaves.

For arcs with similar field shapes at all angles, high dose rate and high speed of drum rotation can be applied resulting in less overall beam time.

An advantage of this system is that there is no rotation of the patient support 6 during the rotation of the drum. There is also no theoretical reason why an oblique entry angle should be required for the treatment, although this may be desirable as a result of planning considerations not related to the required dose distribution. Since the treatment does not require movement of the patient during rotation of the drum, there is no need for significant access to be provided to the patient and the arrangement of the apparatus according to the invention is particularly suited to this treatment technique.

The apparatus of the invention therefore preferably includes controlling means (not shown) for providing a first beam of a first fixed intensity and for controlling the multi-leaf collimator during rotation of the drum, and for providing a second beam of a second fixed intensity and controlling the multi-leaf collimator during the second rotation of the drum. The first and second intensities may be the same, as in the situation described with reference to FIG. 13, although different intensities may be adopted.

Where the apparatus of the invention is for curative treatment and an advanced treatment is to be administered, the apparatus is thus preferably adapted to the above described advanced treatment technique. In such a case, the controlling means must apply, in succession, a number of fixed intensity beams to correspond to the number of rotation arcs required. This depends upon the dose intensity distribution to be administered.

From reading the present disclosure, other modifications and variations will be apparent to persons skilled in the art. Such modifications arid variations may involve other features which are already known in the art and which may be used instead of or in addition to features already described herein. Although claims have been formulated in this application to particular combinations of features, it should be understood that the scope of the disclosure of the present application also includes any novel feature or combination of features disclosed herein either explicitly or implicitly, whether or not relating to the same invention as presently claimed in any claim and whether or not it mitigates any or all of the same technical problems as does the presently claimed invention. The applicants hereby give notice that new claims may be formulated to such features and/or combinations of such features during prosecution of the present application or of any further application derived therefrom.

We claim:

1. Apparatus for treating a patient by exposing a treatment area of the patient to radiation, the apparatus comprising:
    a support;
    a hollow body having a central aperture which defines a passageway extending through the body, the hollow body being mounted to the support so as to be rotatable about a central axis of the hollow body;
    a radiotherapy source mounted to the hollow body so as to be rotatable with the hollow body and for projecting a radiotherapy beam within the passageway which crosses the central axis of the hollow body;
    a beam limiting device for controllably partially limiting the projected area of the beam; and
    a patient support having a generally planar elongated top for receiving the patient and which extends at least partly through the passageway and which is positioned such that an unlimited projection area of the beam substantially covers the treatment area of the patient, said patient support being angularly movable about an axis generally perpendicular to the top of the patient support, thereby allowing the patient support to extend obliquely through the passageway.

2. Apparatus as claimed in claim 1, wherein the radiotherapy source includes a linear particle accelerator disposed within the hollow body which extends in a plane which lies substantially perpendicular to a longitudinal axis of the patient support.

3. Apparatus as claimed in claim 2, wherein the passageway is substantially cylindrical and the apparatus further comprises deflecting means for deflecting the particle beam produced by the linear accelerator to a substantially radial direction with respect to the cylindrical passageway.

4. Apparatus as claimed in claim 1, wherein the patient support is coupled to the hollow body, the coupling being arranged to allow angular movement of the patient support about the rotation axis of the hollow body and means is provided for maintaining the patient support at a substantially constant attitude with respect to a fixed reference plane.

5. Apparatus as claimed in claim 4, wherein the coupling is arranged to allow translational movement of the patient support with respect to the body in one or more directions parallel to or perpendicular to an axis of projection of the beam.

6. Apparatus as claimed in claim 1, further comprising an imaging radiation source which is mounted on the hollow body, and a radiation detection device mounted on the hollow body at a location which is opposite to the imaging radiation source.

7. Apparatus for treating a patient by exposing a treatment area of the patient to radiation, the apparatus comprising:
    a support;
    a hollow body having a central aperture which defines a passageway extending through the body, the hollow body being mounted to the support so as to be rotatable about a central axis of the hollow body;
    a radiotherapy source mounted to the hollow body so as to be rotatable with the hollow body and for projecting a radiotherapy beam within the passageway which crosses the central axis of the hollow body;
    a beam limiting device for controllably partially limiting the projected area of the beam; and
    a patient support for receiving the patient and which extends at least partly through the passageway and which is positioned such that an unlimited projection area of the beam substantially covers the treatment area of the patient, wherein the hollow body comprises an inner portion within which is defined the passageway, and an outer portion, the inner and outer portions being rotatable with respect to each other, the radiotherapy source being mounted on the outer portion of the hollow body, and the beam limiting device being mounted on the inner portion of the hollow body.

8. Apparatus as claimed in claim 7, wherein an imaging source is mounted on the outer portion of the hollow body at a position displaced from the radiotherapy source, the relative rotation between the two portions enabling the radiotherapy source or the imaging source to be aligned with the beam limiting device.

9. Apparatus as claimed in claim 8, wherein the imaging source comprises a light source.

10. Apparatus as claimed in claim 8, wherein the imaging source comprises an X-ray source, and the apparatus further comprises an X-ray image detecting device mounted on the inner portion of the hollow body, opposite to the beam limiting device.

11. Apparatus as claimed in claim 10, wherein the X-ray image detecting device is slidably received by the inner portion of the hollow body so as to be slidable between a first position opposite to the beam limiting device and a second position displaced from the first position, the angle of displacement between the two positions corresponding to the angle of displacement between the imaging source and the radiotherapy source.

12. Apparatus as claimed in claim 1, in which the beam limiting device comprises a multi-leaf collimator.

13. Apparatus as claimed in claim 1, comprising controlling means for controlling the radiotherapy source to provide a first beam of a first fixed intensity and controlling the beam limiting device to selectively limit the projection area of the beam at a plurality of positions of the hollow body during a first rotation of the hollow body, and for controlling the radiotherapy source to provide a second beam of a second fixed intensity and controlling the beam limiting device to selectively limit the projection area of the second beam at a plurality of positions of the hollow body during a second rotation of the hollow body.

14. Apparatus as claimed in claim 1 for treatment by radiotherapy, the treatment involving administering a plurality of arc treatments, each arc treatment corresponding to a rotation of the hollow body and each arc treatment involving administering a beam of a respective fixed intensity, which beam changes shape as the hollow body rotates, the change in shape being governed by the beam limiting device.

15. A transportable radiotherapy system comprising a vehicle having a compartment housing an apparatus for treating a patient as claimed in claim 1.

16. A method of operating an apparatus including a hollow body rotatable about a central axis of the body, a radiotherapy source mounted to the hollow body so as to rotate with the hollow body for protecting a radiotherapy beam within a passageway of the hollow body for receiving a part of a patient, and a beam limiting device for limiting a projection area of the radiotherapy beam said method, comprising:

driving the radiotherapy source to produce a radiotherapy beam of a first fixed intensity;

rotating the hollow body so that it follows a first arc and controlling the beam limiting device so as to alter the projection area of the beam during a first rotation of the hollow body;

driving the radiotherapy source to produce a radiotherapy beam of a second fixed intensity;

rotating the hollow body so that it follows a second arc which substantially corresponds to the first arc and controlling the beam limiting device so as to alter the projection area of the beam during a second rotation of the hollow body.

17. A method as claimed in claim 16, wherein first fixed intensity is equal to the second fixed intensity.

18. A method as claimed in claim 16, wherein three or more hollow body rotations are provided.

19. Apparatus as claimed in claim 2, wherein the patient support is coupled to the hollow body, the coupling being arranged to allow angular movement of the patient support about the rotation axis of the hollow body and means is provided for maintaining the patient support at a substantially constant attitude with respect to a fixed reference plane.

20. Apparatus as claimed in claim 3, wherein the patient support is coupled to the hollow body, the coupling being arranged to allow angular movement of the patient support about the rotation axis of the hollow body and means is provided for maintaining the patient support at a substantially constant attitude with respect to a fixed reference plane.

* * * * *